United States Patent [19]

Weber-Unger et al.

[11] Patent Number: 5,092,881
[45] Date of Patent: Mar. 3, 1992

[54] ARTIFICIAL BREAST

[75] Inventors: Georg Weber-Unger, Kufstein, Austria; Tertulin Eberl, Penzberg, Fed. Rep. of Germany

[73] Assignee: Anita Spezialmiederfabrik Dr. Helbig GES.m. b. H & Co. KG, Kufstein, Austria

[21] Appl. No.: 654,298

[22] Filed: Feb. 4, 1991

Related U.S. Application Data

[63] Continuation of Ser. No. 410,857, Sep. 22, 1989.

[30] Foreign Application Priority Data

Feb. 27, 1989 [DE] Fed. Rep. of Germany ... 8902304[U]

[51] Int. Cl.⁵ ............................................. A61F 2/12
[52] U.S. Cl. .................................... 623/8; 450/54
[58] Field of Search .................. 623/8; 450/54, 55

[56] References Cited

U.S. PATENT DOCUMENTS 4,125,117  11/1978  Lee ......................................... 450/54
4,199,825  4/1980  Knoche .................................. 450/55

FOREIGN PATENT DOCUMENTS 0005035  7/1955  Fed. Rep. of Germany .......... 623/7
8601997  4/1986  PCT Int'l Appl. ..................... 623/8

Primary Examiner—Randy C. Shay
Attorney, Agent, or Firm—Zarley, McKee, Thomte, Voorhees & Sease

[57] ABSTRACT

An artificial breast consists of a soft-elastic dish-shaped plastic body (1) which is symmetrical with respect to a symmetry plane (SE) passing through its tip (3). It has a lateral extension (5) and also a pair of further extensions (6, 7) which lie opposite each other and are arranged on either side of the symmetry plane (SE). The distance ($L_2$) of the ends (6a, 7a) of the further extensions (6, 7) from the symmetry plane (SE) is smaller than the distance ($L_1$) of the end (5a) of the lateral extension (5) from the Z axis which lies in the symmetry plane (SE) and passes through the tip (3). When the artificial breast is worn in a brassiere the lower extension (7) is pushed upwardly by the supporting force of the brassiere and the softness of the prosthesis material while the upper extension (6) remains undeformed. The artificial breast can be worn optionally on the right or left body side.

10 Claims, 2 Drawing Sheets

ARTIFICIAL BREAST

This is a continuation of copending application Ser. No. 07/410,857 filed on Sept. 22, 1989.

BACKGROUND OF THE INVENTION

The invention relates to an artificial breast for wearing in a brassiere or the like consisting of a soft-elastic dish-shaped plastic body which comprises a depression on the rear side of the prosthesis and which is symmetrical with respect to a symmetry plane passing through its tip arranged on the front side of the prosthesis and lying perpendicular to its base surface, has a main part comprising the tip and a lateral extension adjoining the main part and traversed by the symmetry plane and tapering to its end lying in the symmetry plane.

The form of such an artificial breast is known in practice as drop-shaped and is disclosed for example in DE-GM 6,926, 549. It is suitable for women who have had to undergo a less radical mastectomy in which apart from the mamma the lymph nodes have been operatively removed. When such a prosthesis is worn the lateral extension extends in the direction of the armpit and ensures a smooth transition between the prosthesis and the body of the wearer in the region of the armpit. The advantage of the drop-shaped prosthesis resides in that because of its symmetrical form it can be worn optionally on the left or right breast side. It has however the disadvantage that above the mamma it cannot compensate for operatively removed breast tissue and in this region is also unable to provide a smooth transition between the prosthesis surface and the body of the wearer.

Artificial breasts are also known which are likewise made symmetrical so they can be worn on the right or left and which have a lateral extension and an upper extension for providing a smooth transition between the prosthesis and the part of the body lying above the mamma. These artificial breasts have a heart shape, the upper extension and the lateral extension being of equal size. The lateral extension of the heart-shaped prosthesis is however substantially smaller than the lateral extension of the drop-shaped prosthesis because the upper extension must not exceed a predetermined length since otherwise it would project out of the brassiere. The size of the upper extension thus governs the size of the lateral extension which however is then often too small to compensate for operatively removed lymphatic node tissue.

Hitherto, the ideal form of an artificial breast was achievable only with an asymmetric breast prosthesis, the upper extension being smaller than the lateral extension. It is obvious that such a breast prosthesis can be worn only on one side of the body and for the other side of the body a differently formed prosthesis must be used. Compared with symmetrical artificial breasts, asymmetrical artificial breasts are fundamentally more expensive because they must be formed differently for the right and left body side and involve twice as much storage.

The problem underlying the invention resides in further developing the symmetrical artificial breast according to the preamble in such a manner that it provides both a smooth transition to the armpit region of the wearer with simultaneous complete compensation of removed lymphatic node tissue and in addition provides a smooth transition to the body part of the wearer lying above the mamma.

SUMMARY OF THE INVENTION

The problem of the invention is solved in that the main part is followed by a pair of further extensions which lie opposite each other and which are arranged on either side of the symmetry plane and taper towards their respective end which is spaced from the symmetry plane a distance which is smaller than the distance between the end of the lateral extension and a Z axis which passes in the symmetry plane perpendicularly to the base area through the tip of the plastic body.

The artificial breast according to the invention unites all the advantages of a symmetrical artificial breast with those of an asymmetrical artificial breast, the respective lower extension having no disadvantages for the wearer. As has surprisingly been found in tests when the prosthesis is worn the lower extension is pushed upwardly by the support force exerted due to the weight of the prosthesis onto the lower extension and the softness of the prosthesis material, the lower extension thereby adapting itself to the form of the brassiere and the depression on the rear side of the prosthesis being correspondingly deformed whilst the upper extension remains undeformed and fully retains its function of simulating the upper breast root.

The prosthesis according to the invention further has the advantage that when worn it is still further adapted to the form of the natural breast because the upwardly pushed lower extension has a curvature equal to that of the natural breast in the lower breast region and like the natural breast in the lower breast region forms a fold with the body part lying beneath the breast.

Advantageously, each of the further extensions has an area which is smaller than the area of the lateral extension. As a result, in conjunction with the selection of the lengths of the extensions according to the invention symmetry is retained and the upper extension cannot project out of the brassiere, the lateral extension being large enough to compensate for operatively removed lymphatic node tissue and provide a smooth transition to the armpit of the wearer.

Further advantageous developments of the invention are set forth in subsidiary claims 3 and 4.

A substantial advantage of the prosthesis according to the invention is that it can be worn optionally on the right or left breast side and is therefore cheaper because of simplified production and storage.

BRIEF DESCRIPTION OF THE DRAWINGS

An example of the embodiment of the invention will be described hereinafter in detail in the drawings, wherein.

DESCRIPTION OF THE PREFERRED EMBODIMENT

Figure 1:
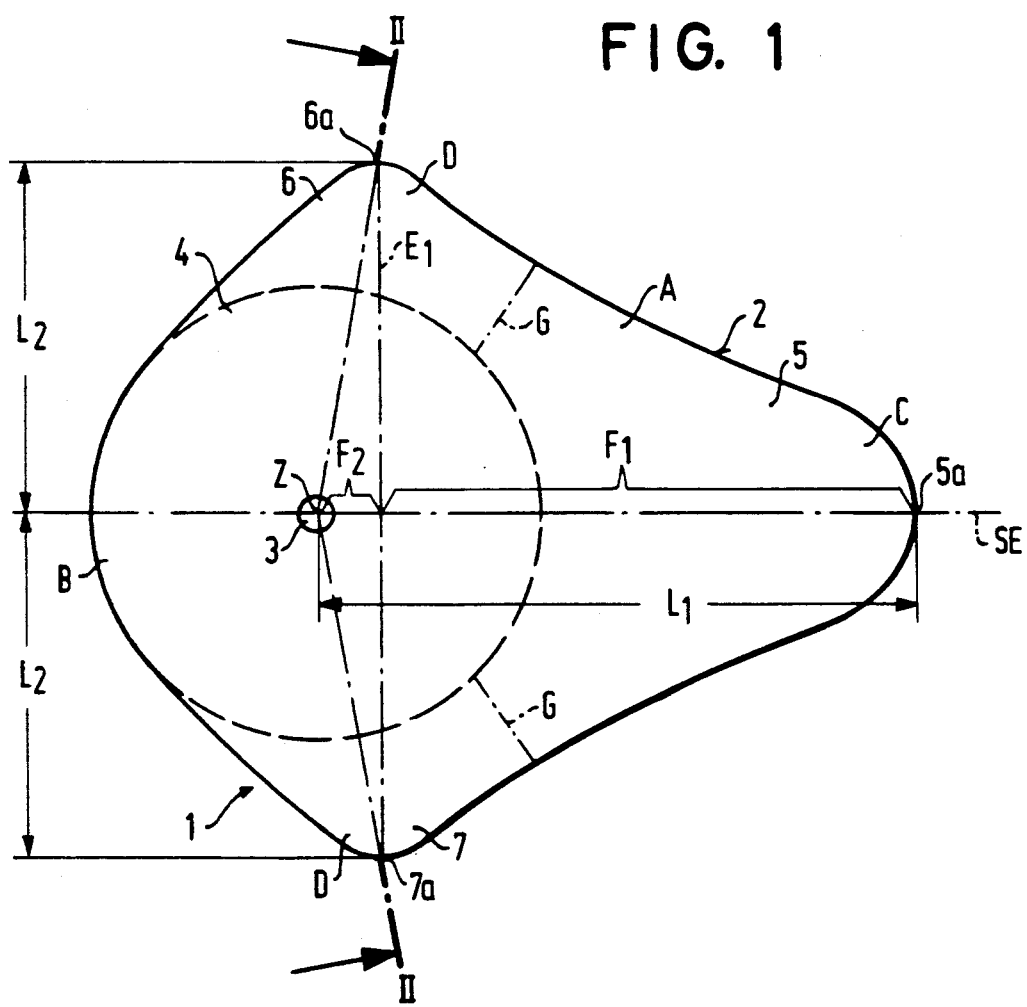
FIG. 1 is a plan view of the front side of the artificial breast according to the invention.

An artificial breast according to the invention consists of a soft-elastic dish-shaped plastic body 1 which consists essentially of an addition-crosslinked gel-like silicone rubber mass which is enclosed by a two-part plastic sheet, for example polyurethane sheet, the two sheet parts being welded together along the prosthesis edge 2. As apparent from FIGS. 1 and 2 the plastic body 1 has a form which is symmetrical with respect to a symmetry plane SE passing through its tip 3 and perpendicular to its base area A. The plastic body 1 consists of a main part 4 having the tip 3 and a substantially circular base area B, the surrounding circle of which is shown in FIG. 1 in dashed line in so far as it lies within the overall base area A of the plastic body 1. The tip 3 of the plastic body 1 is arranged on the front side of the prosthesis and has the form of a breast nipple.

Figure 3:
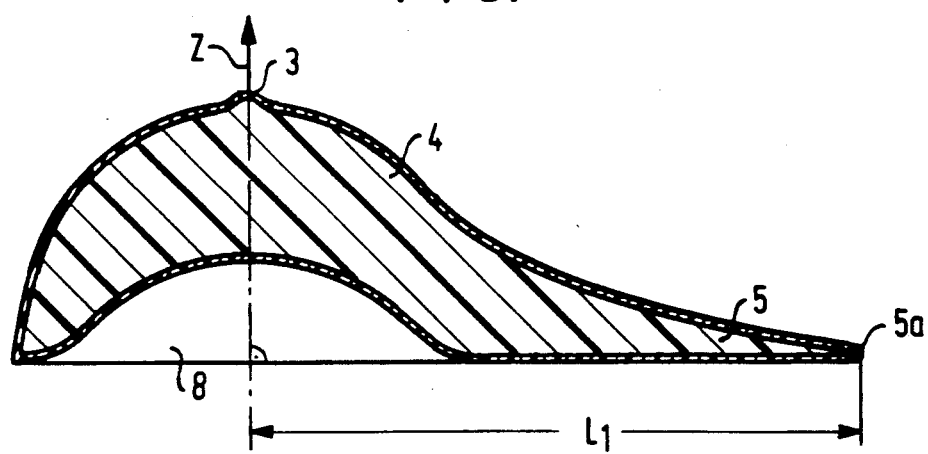

The main part 4 is followed by a lateral extension 5 through which the symmetry plane SE passes and which with increasing distance from the main part 4 taper in its base area C to an end 5a and which as shown in FIG. 3 perpendicularly to its base area C becomes outwardly flatter.

The front side of the plastic body 1 has a convex form simulating a natural breast whilst the rear side has a depression 8 which is arched somewhat flatter than the front side of the prosthesis. The plastic body 1 therefore has overall a dish shape.

The main portion 4 is adjoined on either side of the symmetry plane SE by an upper and lower extension 6 and 7 respectively which lie exactly opposite each other, i.e. the ends 6a and 7a lie in a common first plane which intersects the symmetry plane at right-angles along a line which is not shown which is spaced from the Z axis passing through the tip 3 a distance $F_2$ which is smaller than the distance $F_1$ of the end 5a of the lateral extension 5 from said line. The upper and lower extensions 6 and 7, which because of the symmetry of the plastic body 1 with respect to the symmetry plane SE have the same size and shape, taper in their base area D towards their ends 6a and 7a and perpendicularly to their base area D become outwardly flatter. The approximate boundaries between the base areas D and the base area C are indicated in FIG. 1 in each case by a dot-dash line G.

As apparent from FIG. 1, the end 6a of the upper extension 6 and the end 7a of the lower extension 7 have the same distance $L_2$ from the symmetry plane SE which is less than the distance $L_1$ of the end 5a of the lateral extension 5 from the Z axis which lies in the symmetry plane SE, is perpendicular to the base area A and passes through the tip 3. In addition, the upper and lower extensions 6 and 7 each have a smaller base area D than the lateral extension 5.

The main part 4 has an end 4a opposite to the end 5a of the lateral extension 5, said end 4a being spaced from the common first plane a distance $L_3$ which is smaller than the distance $L_2$.

Figure 2:
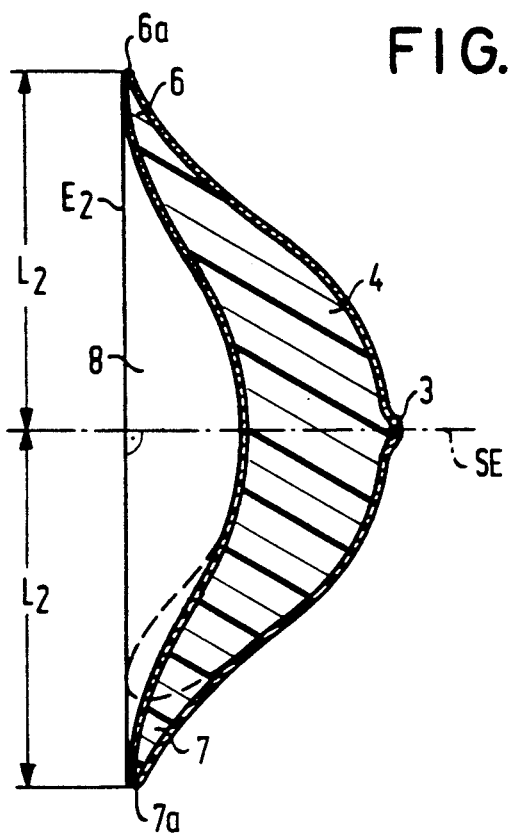
FIG. 2 is a section through the artificial breast shown in FIG. 1 along the line II—II and FIG. 3 is a section of the artificial breast shown in FIG. 1 along the plane of symmetry SE.

As apparent from FIG. 2 the ends 6a and 7a of the extensions 6 and 7 respectively lie in a second common plane defining the rear side of the prosthesis.

In FIG. 2, in dashed line the form is shown which the lower extension 7 and the adjoining outer region of the main part 4 assume when the artificial breast is carried in a brassiere. The support force of the brassiere exerted on the lower extension 7 due to the weight of the prosthesis pushes the lower extension upwardly, said extension adapting itself to the form of the brassiere and the hollow or depression 8 present on the rear side of the prosthesis being correspondingly deformed. The deformation of the lower extension 7 when the prosthesis is worn in a brassiere does not influence the form of the remaining parts of the prosthesis. When the lower extension 7 is pushed upwardly it has the same degree of curvature as the natural breast in the lower breast region and forms like the natural breast a fold with the adjoining body part beneath the breast.

Due to the symmetrical configuration of the prosthesis according to the invention with respect to the symmetry plane SE it can be worn on appropriate alignment optionally on the right or left side of the body.

The form and arrangement of the extensions is not restricted to the example of embodiment but can be modified within wide limits as long as the symmetry of the plastic body with respect to the symmetry plane SE is retained. Thus, it is for example possible for the ends of the upper and lower extensions to lie in a common first plane which intersects the symmetry plane along the Z axis at right-angles.

We claim:

1. Breast prosthesis for wearing in a brassiere or the like, said prosthesis having a rear side and a front side opposite said rear side and a tip arranged on said front side, and comprising a soft-elastic dish-shaped plastic body which has a base area and a symmetry plane passing through said tip and extending perpendicularly to said base area, said plastic body being symmetrical with respect to said symmetry plane and comprising:

a depression on said rear side to form said prosthesis into a convex shape with the tip located at the apex thereof;

a main part surrounding said tip and having an outer end spaced from said tip and traversed by said symmetry plane, said tip being centrally located on the main part;

a lateral extension adjoining said main part and traversed by said symmetry plane, said lateral extension having an end traversed by said symmetry plane;

a pair of upper and lower extensions adjoining said main part and being arranged on opposite sides of said symmetry plane, each of said pair of upper and lower extensions having a respective end which is spaced from said symmetry plane a first distance which is smaller than a second distance between said end of said lateral extension and a Z-axis which passes in said symmetry plane perpendicularly to said base area through said tip of said plastic body, each of said lateral extension and said pair of upper and lower extensions tapering to its respective end, said ends of said upper and lower extensions being traversed by a first plane which intersects said symmetry plane, wherein said lower extension is pushed upwardly by said brassiere when the prosthesis is worn in said brassiere, and said outer end of said main part being spaced from said first plane by a third distance which is smaller than said first distance; and said first plane intersecting said symmetry plane at right angles along a line which is spaced from said Z-axis a fourth distance and extends between said Z-axis and said end of said lateral extension, said fourth distance being less than a fifth distance by which said end of said lateral extension is spaced from said line.

2. Breast prosthesis according to claim 1, wherein each of said lateral extension and said pair of upper and lower extensions has a respective base area and said base area of each of said lower and upper extensions is smaller than the base area of said lateral extension.

3. Breast prosthesis according to claim 1, wherein said ends of said upper and lower extensions lie in a common second plane which extends on said rear side of the prosthesis.

4. A breast prosthesis comprising:

a substantially circular soft elastic body having a rear side and a front side with a nipple-like tip substantially centered on said body, and said body being convexly shaped with the tip being at the apex thereof;

an upper extension having an upper end spaced apart from a longitudinal plane traversing said tip, said upper extension extending upwardly from said body towards said upper end;

a lower extension having a lower end spaced from said longitudinal plane, said lower extension extending downwardly from said body towards said lower end and being flexible so that said lower end is displaced upwardly within a brassiere when the prosthesis is worn in a brassiere;

a lateral extension having a lateral end spaced from a Z-axis lying in said longitudinal plane and projecting through said tip, said lateral extension extending laterally from said body towards said lateral end, said lateral end being spaced from said Z-axis by a distance greater than a distance by which said upper end is spaced from said longitudinal plane;

said upper and lower ends being traversed by a common transverse plane which intersects said longitudinal plane;

said body having an outer end opposite to said lateral end, said outer end being spaced from said transverse plane by a distance which is smaller than said distance by which said upper end is spaced from said longitudinal plane; and said lower end being spaced from said longitudinal plane by a distance substantially equal to that by which said upper end is spaced from said plane when said lower end is not displaced upwardly.

5. The prosthesis of claim 4 wherein the upper extension is tapered from the body to its end so as to provide a smooth transition between the prosthesis and the wearer's body above the mamma.

6. The prosthesis of claim 4 wherein the lateral extension is tapered from the body to its end so as to provide a smooth transition between the prosthesis and the wearer's body toward the armpit.

7. The prosthesis of claim 4 wherein the prosthesis is symmetrical about said longitudinal plane such that the prosthesis can be worn on either the left or right side of the wearer's body.

8. The prosthesis of claim 4 wherein the ends of the upper and lower extensions are positioned laterally from the tip toward the end of the lateral extensions such that a line passing through the ends of the upper and lower extensions is laterally offset from the tip toward the end of the lateral extension.

9. The prosthesis of claim 4 wherein the area encompassed by the upper and lower extensions is smaller than the area encompassed by the lateral extension.

10. The prosthesis of claim 4 wherein the rear side is concave and the front side is convex, the rear side having a radius of curvature which is less than the radius curvature of the front side.

* * * * *